(12) United States Patent
Lin

(10) Patent No.: US 6,730,125 B1
(45) Date of Patent: May 4, 2004

(54) SPINAL FIXATION AND RETRIEVAL DEVICE HAVING SIDE PIECES

(76) Inventor: Chih-I Lin, 14292 Spring Vista La., Chino Hills, CA (US) 91709

( * ) Notice: Subject to any disclaimer, the term of this patent is extended or adjusted under 35 U.S.C. 154(b) by 0 days.

(21) Appl. No.: 09/640,716

(22) Filed: Aug. 18, 2000

(30) Foreign Application Priority Data

Feb. 2, 2000 (TW) ........................................ 89202029 U (51) Int. Cl.$^7$ ................................................. A61F 2/44
(52) U.S. Cl. ................................................. 623/17.11
(58) Field of Search .................... 623/17.11–17.16; 606/61

(56) References Cited

U.S. PATENT DOCUMENTS

| | | | |
|---|---|---|---|
| 5,534,029 A | * | 7/1996 | Shima ..................... 623/17.15 |
| 5,697,977 A | | 12/1997 | Pisharodi ..................... 623/17 |
| 5,888,228 A | | 3/1999 | Knothe et al. ................. 623/17 |
| 5,980,522 A | * | 11/1999 | Koros et al. ................... 606/61 |
| 6,176,882 B1 | * | 1/2001 | Biedermann et al. .... 623/17.15 |

FOREIGN PATENT DOCUMENTS

| | | |
|---|---|---|
| DE | 198 16 832 C | 1/2000 |
| EP | 0 951 879 | 10/1999 |
| WO | WO 98 02117 | 1/1998 |
| WO | WO 98 48738 | 11/1998 |

* cited by examiner

*Primary Examiner*—Bruce Snow
*Assistant Examiner*—Brian E Pellegrino
(74) *Attorney, Agent, or Firm*—Bacon & Thomas (57) ABSTRACT

A spinal fixation and retrieval device comprises a retrieval main body, two side pieces, and a fastening device for fastening substantially symmetrically the two side pieces with two sides of the retrieval main body. The two side pieces are substantially smaller in thickness than the retrieval main body.

4 Claims, 15 Drawing Sheets

FUG.10b

FIG. 10c

SPINAL FIXATION AND RETRIEVAL DEVICE HAVING SIDE PIECES

FIELD OF THE INVENTION

The present invention relates to a spinal fixation and retrieval device having side pieces.

BACKGROUND OF THE INVENTION

The conventional spinal fixation and retrieval device is generally grouped into a spacer category and a cage category. A typical spacer is, for example, the RAMPS serial products made by AcroMed Corporation of the United States. The spacer is defective in design in that they do not become fused with the vertebrae. The cage category may be able to fuse with the vertebrae; nevertheless it is apt to become embedded in the vertebrae in light of the endplate which is implanted in the surgery.

The objective of the present invention is to provide a spinal fixation and retrieval device which has the both functions of an intervertebral spacer and the vertebral cage.

It is another objective of the present invention to provide a spinal fixation and retrieval device having side pieces.

It is still another objective of the present invention to provide a spinal fixation and retrieval device having side pieces capable of a micro-motion in relation to a retrieval main body of the spinal fixation and retrieval device.

SUMMARY OF THE INVENTION

The spinal fixation and retrieval device of the present invention is formed of a retrieval main body and the side pieces. The retrieval main body enables the spinal fixation and retrieval device of the present invention to fuse with the vertebrae. The side pieces prevent the spinal fixation and retrieval device of the present invention from continuing to be embedded into the vertebrae. In addition, the retrieval main body and the side pieces are movably joined together so that they can be selected for use on the basis of the desired size. Further, the relative position/angle between the retrieval main body and the side pieces can be automatically adjusted in accordance with the size/shape of the intervertebral space. Moreover, they have an appropriate micro-motion function, which enhances the healing effect.

DETAILED DESCRIPTION OF THE INVENTION

The spinal fixation and retrieval device comprises:

a retrieval main body;

two side pieces; and a joining means for joining symmetrically the two side pieces with two sides of the retrieval main body.

The present invention is characterized by the side pieces, which have a thickness substantially smaller than a thickness of the retrieval main body.

Preferably, said two side pieces are joined together by a connection portion, and said connection portion is joined with said retrieval main body. More preferably, said connection portion of said two side pieces is a fitting ring for fitting with said retrieval main body.

Preferably, said retrieval main body is joined with said joining means, and said two side pieces are joined with said joining means. More preferably, said two side pieces and said joining means are joined together by a retaining means or a threading means such that said two side pieces are substantially not fastened directly with said retrieval main body Preferably, said retrieval main body is joined with said joining means, and each of said two side pieces has a joining portion connected with a junction of said retrieval main body and said joining means. More preferably, said junction of said retrieval main body and said joining means forms a groove and/or cavity for receiving said joining portions of said two side pieces.

Figure 7A:
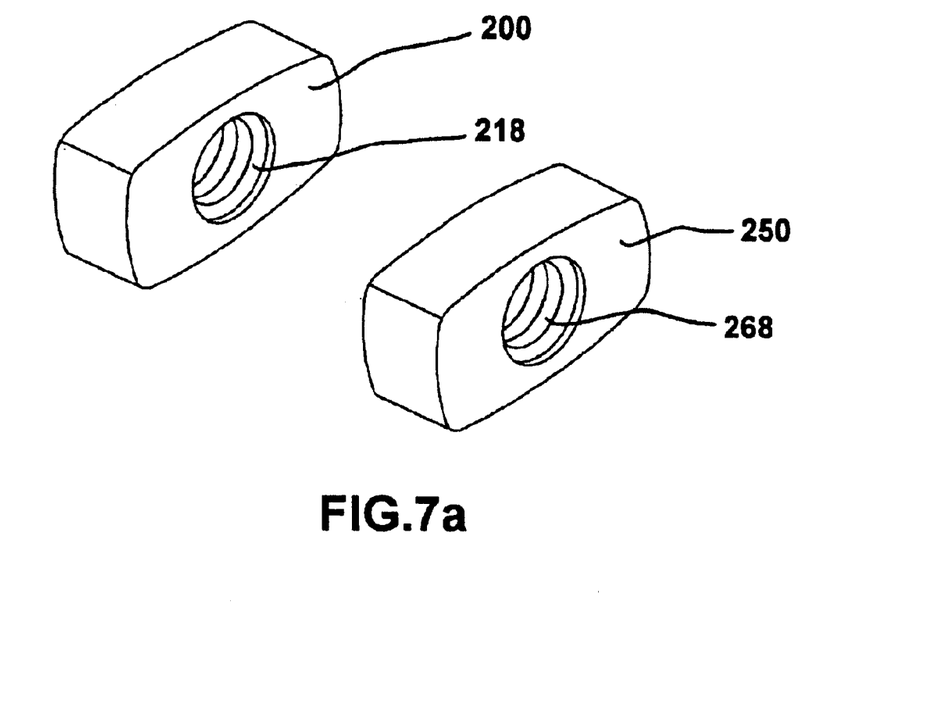
FIGS. 7a–7c are schematic views of the principal components of a fifth preferred embodiment of the present invention.
Figure 7B:
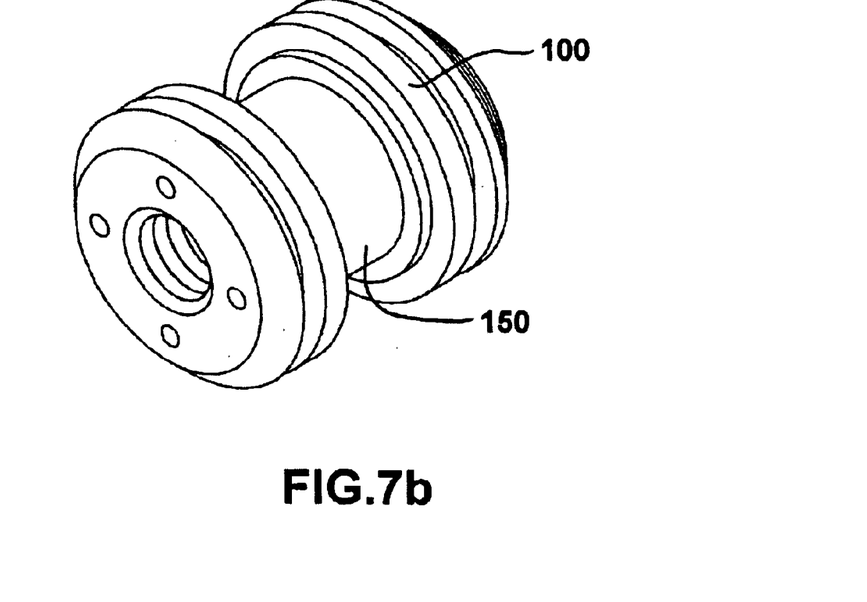

The retrieval main body referred to above may be a conventional vertebral cage, a variation of the conventional vertebral cage or an improved retrieval main body, as shown in FIG. 7b, which has a retaining slot. The retrieval main body may be in a cylindrical shape, a rectangular shape, and the like, preferably the cylindrical shape. The retrieval main body is of a hollow columnar shape and is provided in the surface thereof with a hole in communication with the hollow cavity.

Figure 1A:
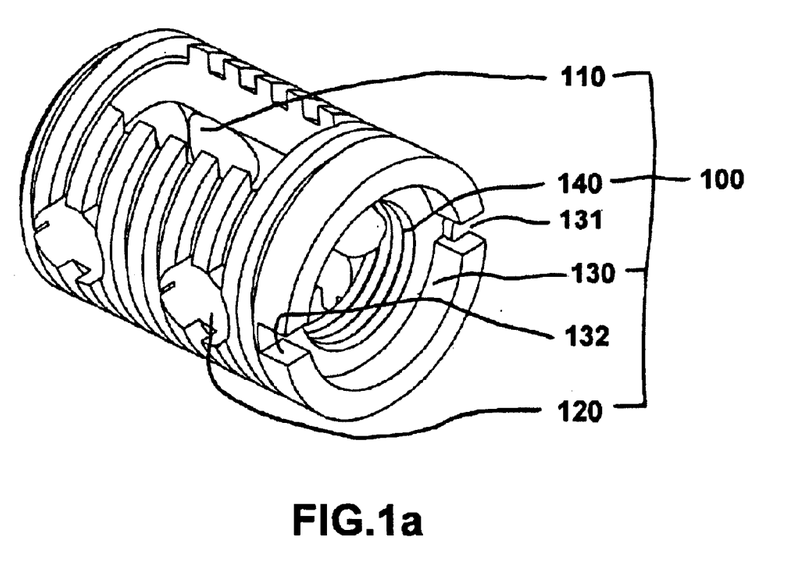
FIGS. 1a–1c are schematic views of principal components of a first preferred embodiment of the present invention.
Figure 1B:
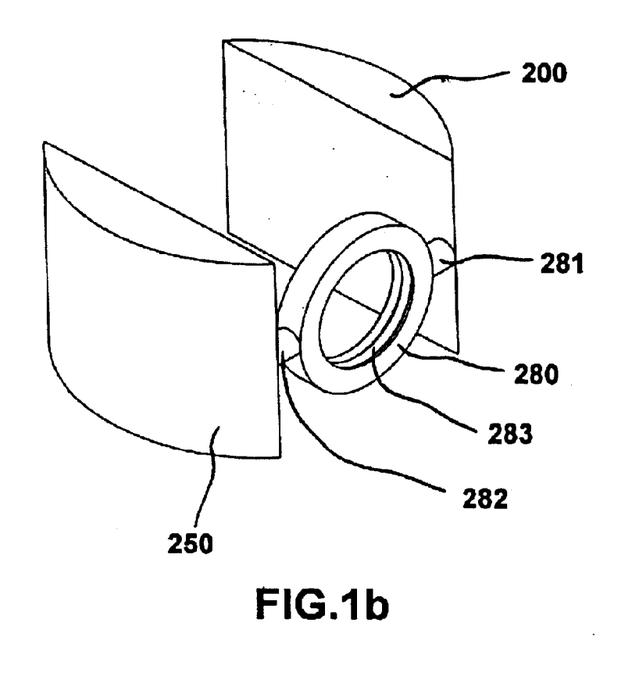

The side pieces referred to above may be two separate side pieces, as shown in FIGS. 4a, 5a, 6a and 7a, or a united body, as shown in FIG. 1b. The side pieces may be of any shape. However, the side pieces have a side which is opposite to the retrieval main body and is preferably arcuate in shape. In addition, the side pieces may be platelike, striplike, barlike, piecelike or bent wire.

The side pieces referred to above are substantially smaller in thickness than the retrieval main body. The thickness refers to the vertical direction of a standing human body into which the side pieces are implanted.

Figure 1C:
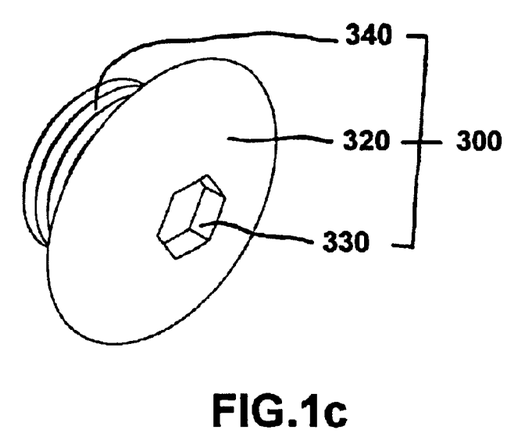
Figure 4A:
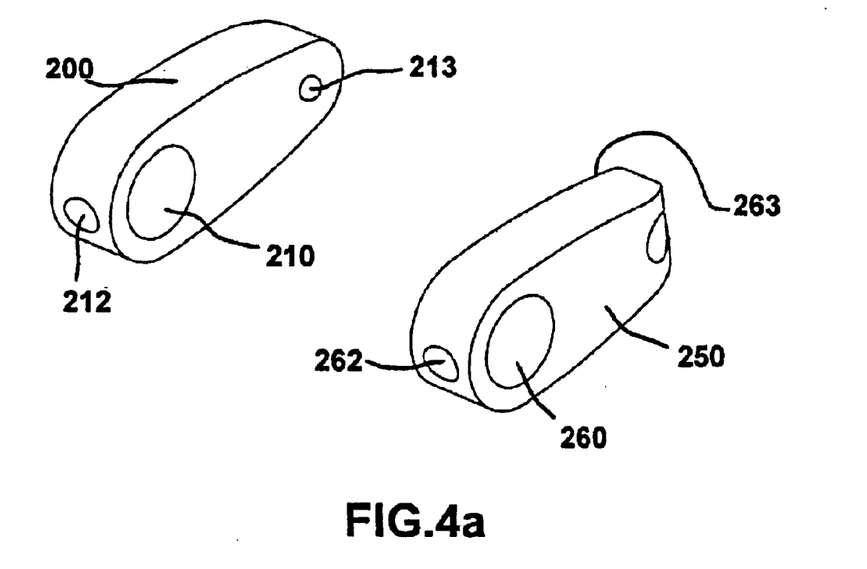
FIGS. 4a–4d are schematic views of the principal components and the assembly of the principal components of a second preferred embodiment of the present invention.
Figure 4B:
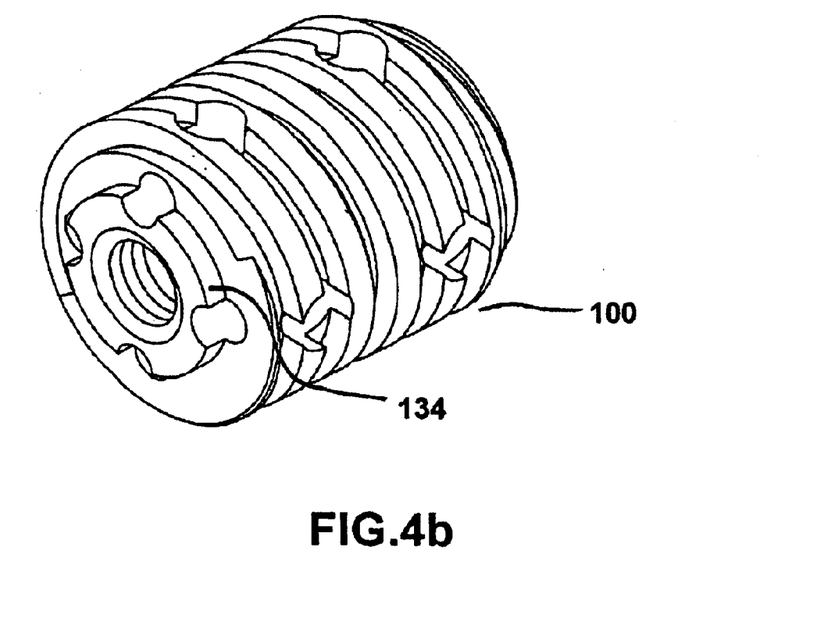
Figure 4C:
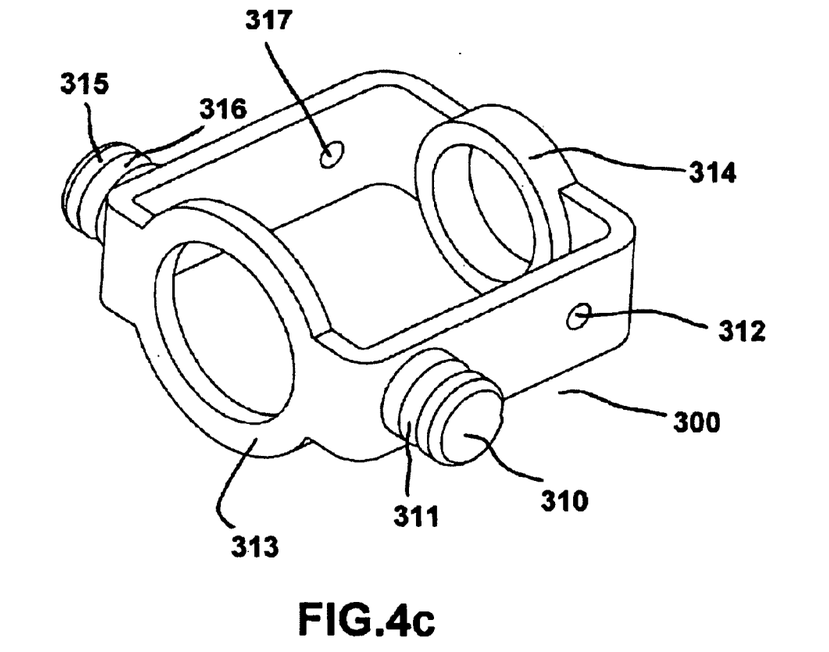
Figure 7C:
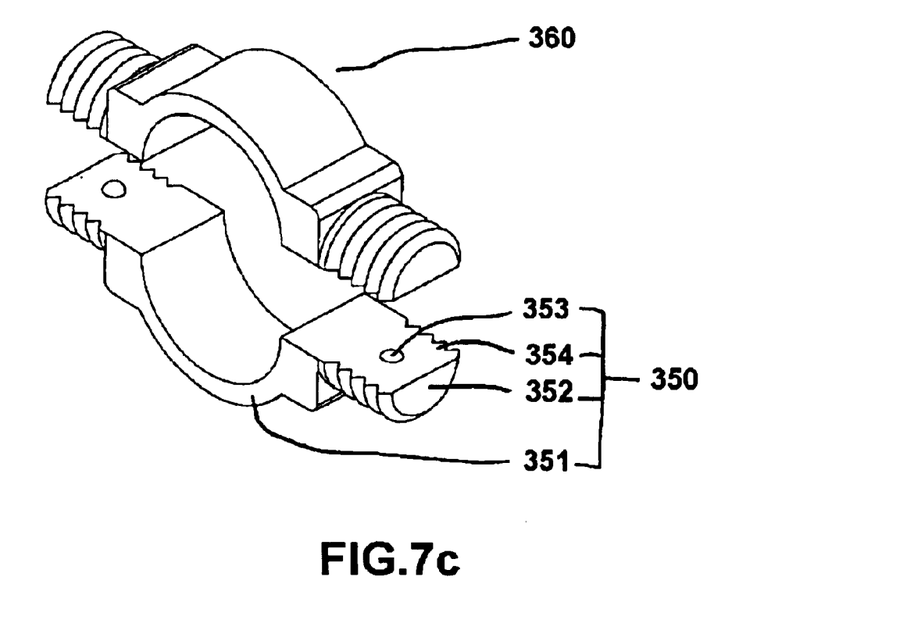

The joining means referred to above is any joining element capable of joining the retrieval main body with the side pieces, such as a nut as shown in FIG. 1c, a joining frame as shown in FIG. 4c, or a fitting ring member as shown in FIG. 7c.

In order to describe further the present invention, the preferred embodiments are described hereinafter with reference to the accompanying drawings.

Figure 2:
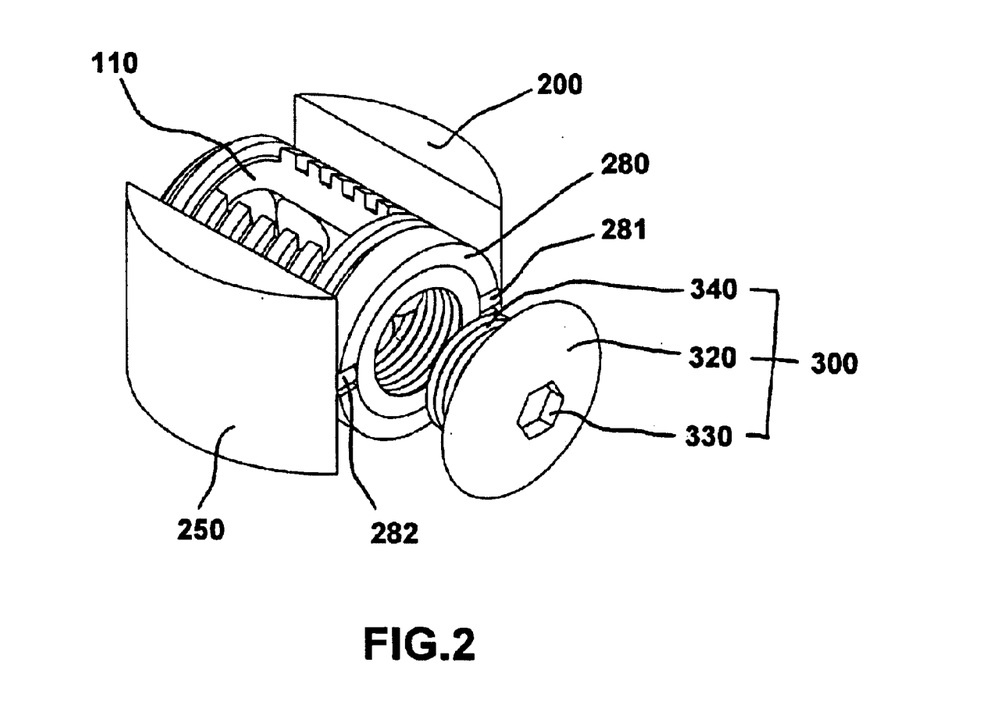
FIGS. 2 and 3 are sequential schematic views of the assembly of the principal components of the first preferred embodiment as shown in FIG. 1.

In FIG. 1a, 100 denotes the retrieval main body. 110 denotes the through hole for inserting the bone graft. 120 denotes a tool hole. 130 denotes a fitting offset. 131 and 132 denote fitting ports. 140 denotes threads. In FIG. 1b, 200 and 250 denote the two side pieces, which are joined together by a connection fitting ring 280 and connection rods 281 and 282, which are respectively fitted into the fitting offset 130 and the fitting ports 131, 132 of the retrieval main body 100, as shown in FIG. 2. In FIG. 1c, 300 denotes the joining means. 320, 330 and 340 denote a joining cover, a tool hole, and threads of the joining means. The threads 340 are used to engage the threads 283 of the connection fitting ring 280 and the threads 140 of the retrieval main body 100, thereby the retrieval main body, the side pieces, and the joining means are united, as shown in FIG. 3.

Figure 3:
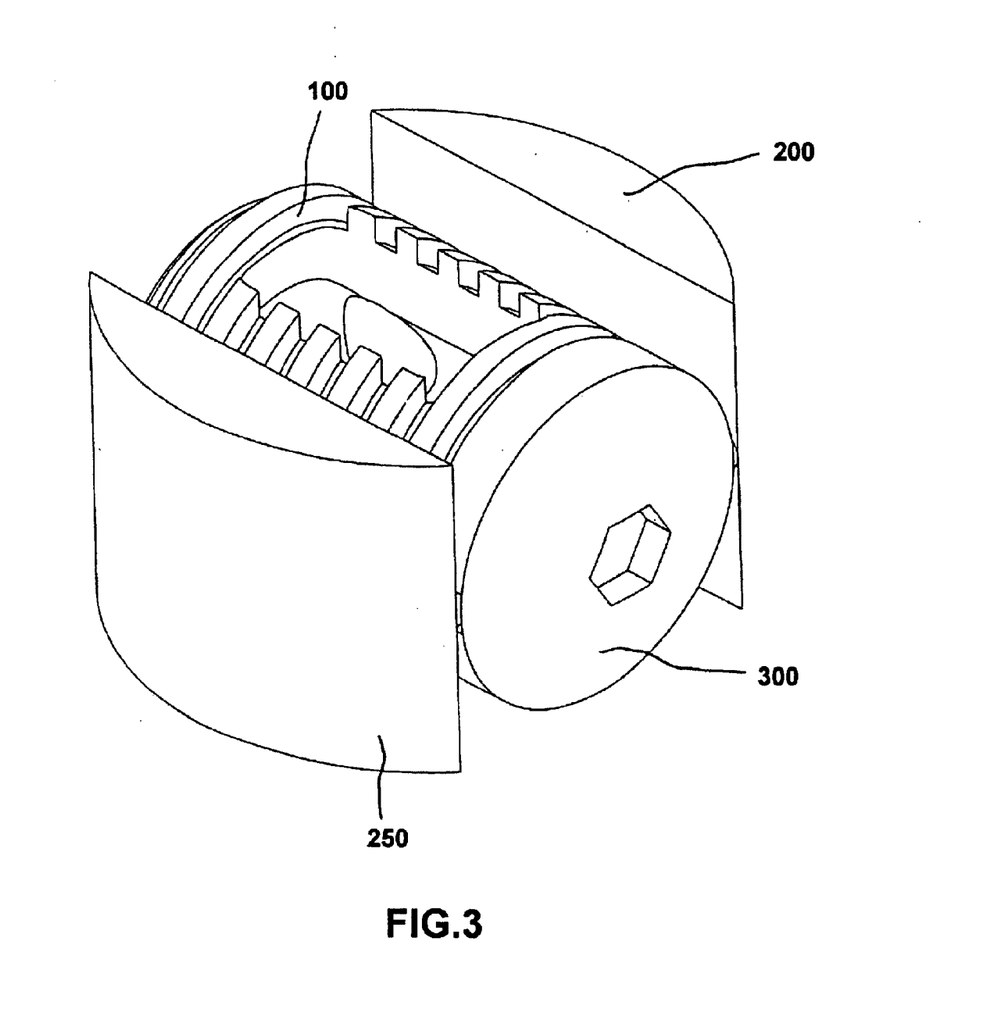

In FIG. 2 and FIG. 3, the reference numerals are similar in definition to those of FIGS. 1a–1c.

Figure 4D:
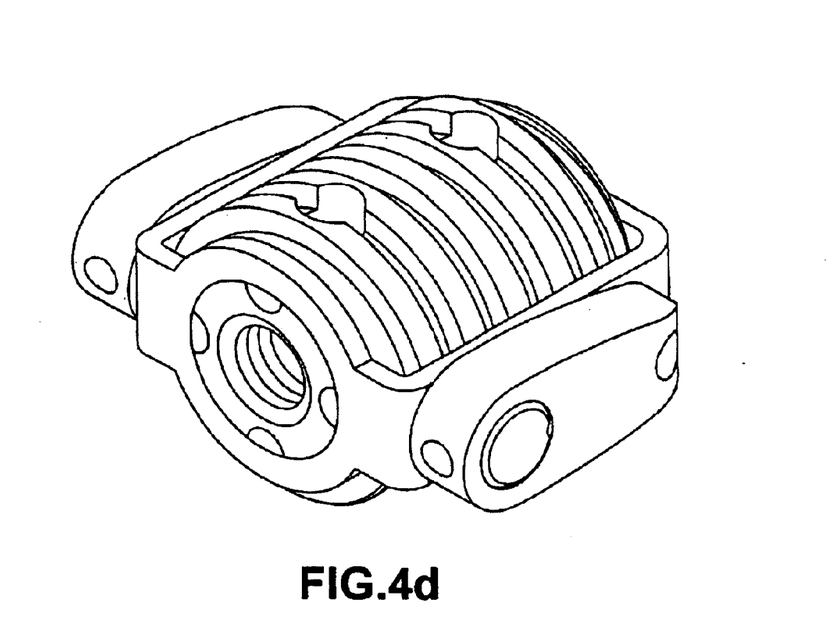

In FIG. 4a, 200 and 250 denote two side pieces. 210 and 260 denote the joining holes of the side pieces. 212 and 262 denote the auxiliary joining holes of the side pieces. 213 and 263 denote the temporary fixation projections. In FIG. 4b, 100 denotes the retrieval main body, and 134 denotes joining protrusion. In FIG. 4c, 300 denotes the joining means. 310(315), 311(316), 312(317), 313, 314 denote respectively the joining bolt, the joining bolt slot, temporary fixation hole, front joining fitting ring, and rear joining fitting ring. The joining process includes the fitting of the rear joining fitting ring 314 into the rear joining fitting offset (not shown in the drawing, but similar in shape to the fitting offset 130 of FIG. 1a, may be replaced by a hole) of the retrieval device main body 100. After slightly pulling the front joining fitting ring 313 outward, it is fitted onto the joining protrusion 134 of the retrieval main body 100. The joining holes 210 and 260 of the two side pieces 200 and 250 are mounted to the joining bolts 315 and 310. The auxiliary joining holes 212 and 262 of the side pieces are gently hammered to result in the protruded points (or small screws are threaded therein), which are retained in the joining bolt slots 316 and 311. Thereafter, the side pieces 200 and 250 are respectively turned on the joining bolts 315 and 310 serving as axes, thereby enabling the temporary fixation protruded points 213 and 263 to fix temporarily on the temporary fixation holes 312 and 317, as shown in FIG. 4d. The temporary fixation protruded points 213 and 263 can be forced by a slight force to detach from the temporary fixation holes 312 and 317 prior to use.

FIG. 3 shows the spinal fixation and retrieval device, in which the two side pieces are substantially incapable of rotation in relation to the retrieval main body in view of the fact that the connection rods 281, 282 of the side pieces are fitted into the fitting ports 131 and 132 of the retrieval main body 100. However, the side pieces are capable of a micro-motion in relation to the connection rods 281 and 282. As shown in FIG. 4, the joining means 300 of the spinal fixation and retrieval device can be turned at any angle in relation to the retrieval main body 100. The side pieces 200 and 250 are capable of turning on the joining bolts 315 and 310 serving as axes.

Figure 5A:
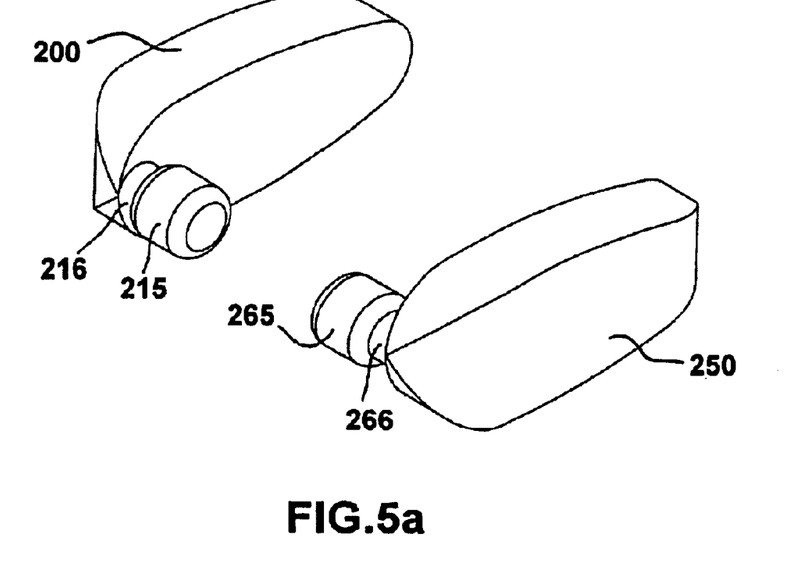
FIGS. 5a–5d are schematic views of the principal components and the assembly of the principal components of a third preferred embodiment of the present invention.
Figure 5B:
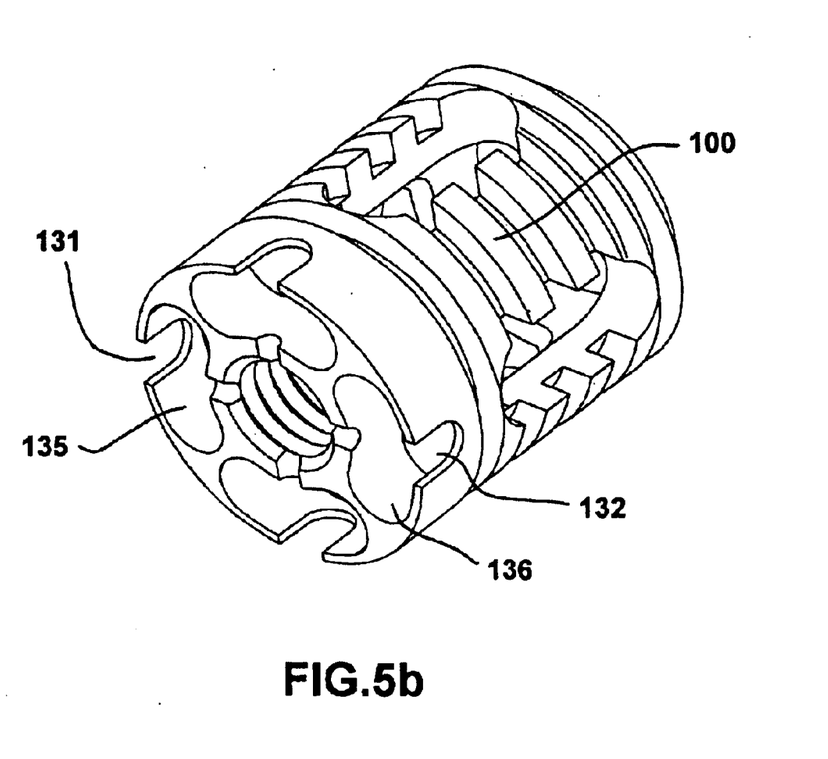
Figure 5C:
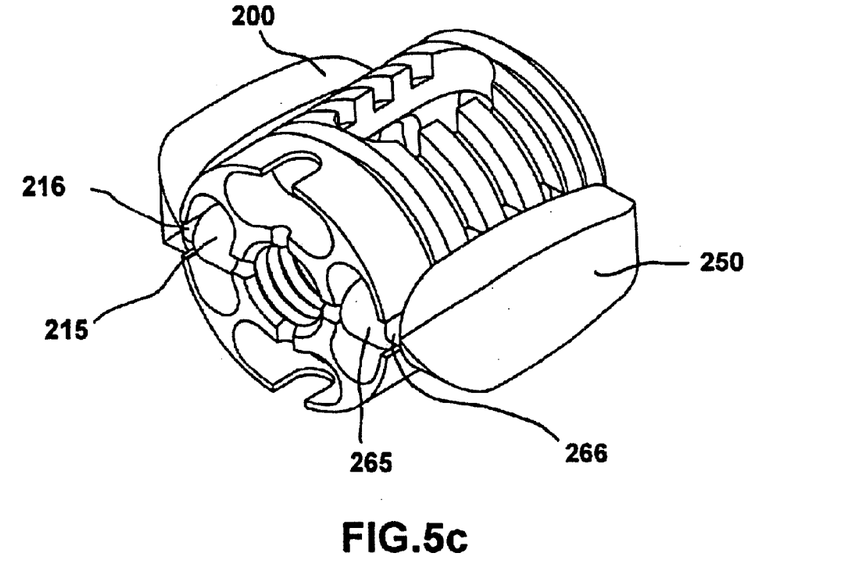
Figure 5D:
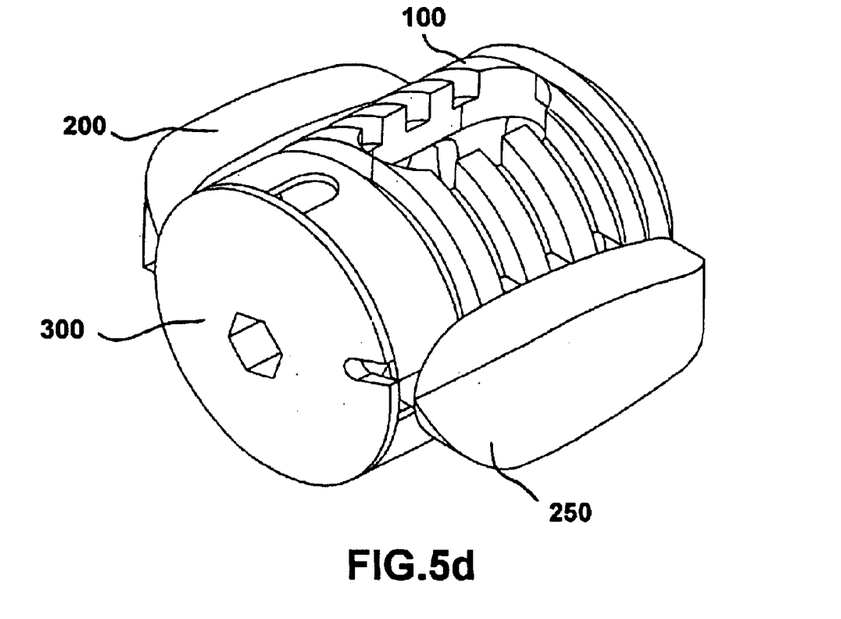

In FIG. 5a, 200 and 250 denote two side pieces. 215 and 265 denote the connectors of the two side pieces 200 and 250. 216 and 217 denote the connection necks of the connectors 215 and 265. In FIG. 5b, the reference numerals 100, 131 and 132 are similar in definition to those of FIG. 1a; and 135 and 136 denote the fitting slots for fitting the connectors 215 and 265. The connectors 215 and 265 are fit in the fitting slots 135 and 136, while the connection necks 216 and 266 are receiving in the fitting ports 131 and 132, as shown in FIG. 5c. Thereafter, the joining means 300 and the retrieval main body 100 are fastened together, as shown in FIG. 5d. The reference numerals in FIG. 5d are similar in definition to those of FIGS. 5a and 5b.

Figure 6A:
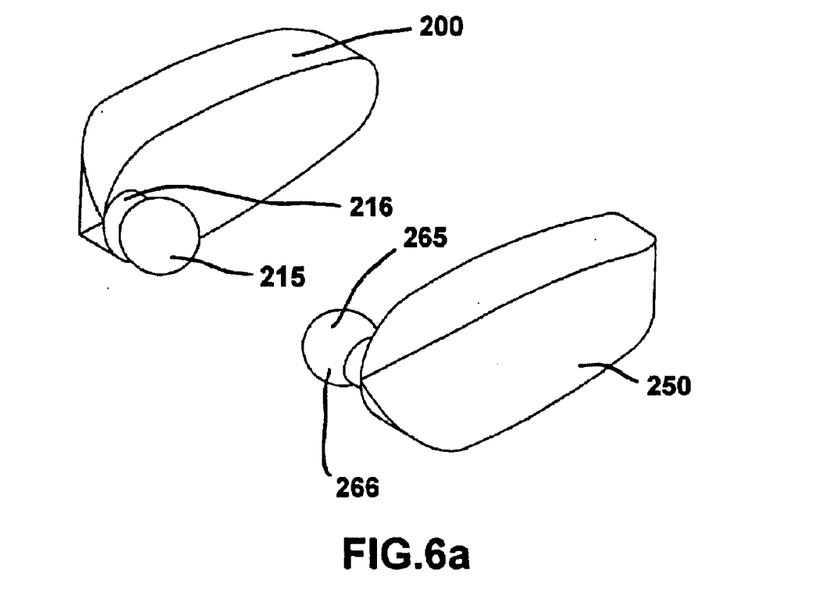
FIGS. 6a–6d are schematic views of the principal components and the assembly of the principal components of a fourth preferred embodiment of the present invention.
Figure 6B:
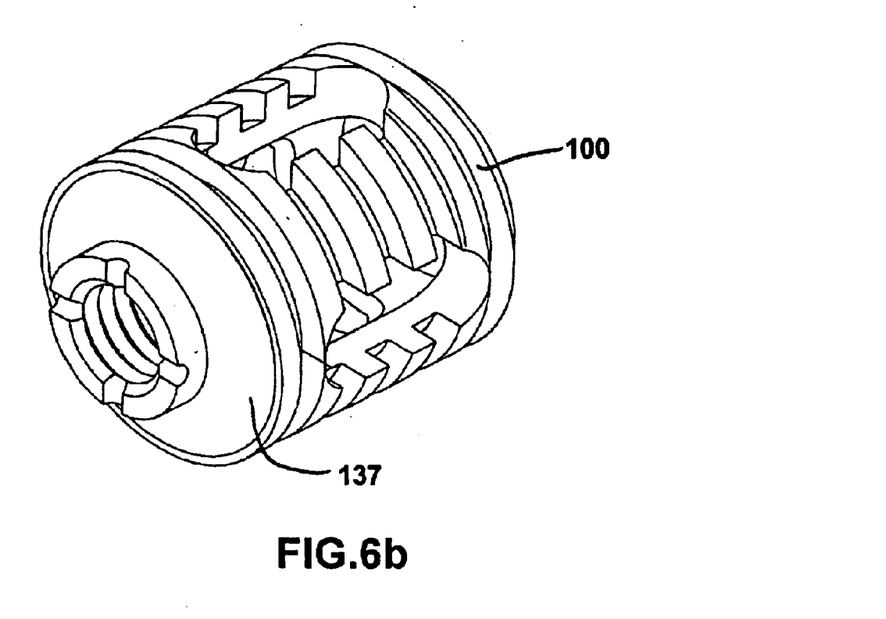
Figure 6C:
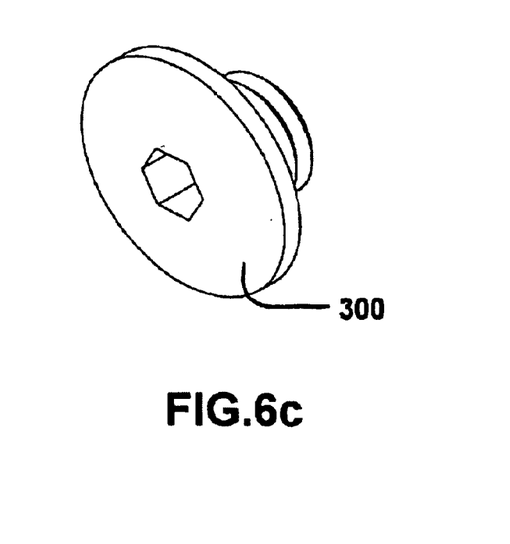

The spinal fixation and retrieval device shown in FIGS. 6a–6d are similar to FIGS. 5a–5d, wherein like elements and parts are designated by like numerals. With the exception of a fitting groove 137 is provided on the retrieval main body 100, as shown in FIG. 6b. In addition, the connectors 215 and 265 of the side pieces 200 and 250 are spherical in shape. The joining means 300 is recessed for forming jointly with the fitting groove 137 of the retrieval main body 100 an annular fitting groove which has an oval or round cross section, thereby the connectors 215 and 265 can be rotatably fit in the annular fitting groove between the retrieval main body 100 and the joining means 300.

Figure 6D:
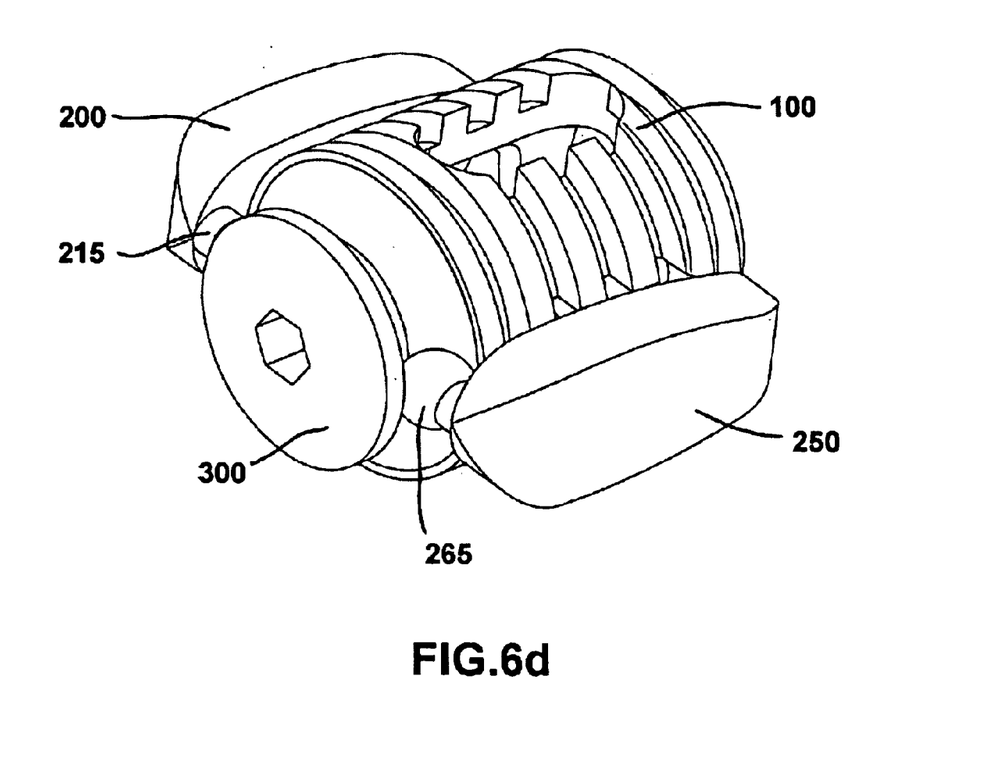

FIG. 5d shows a spinal fixation and retrieval device whose two side pieces are substantially incapable of rotation in relation to the retrieval main body. FIG. 6d shows a spinal fixation and retrieval device whose side pieces are capable of turning or twisting in relation to the retrieval main body.

Figure 8A:
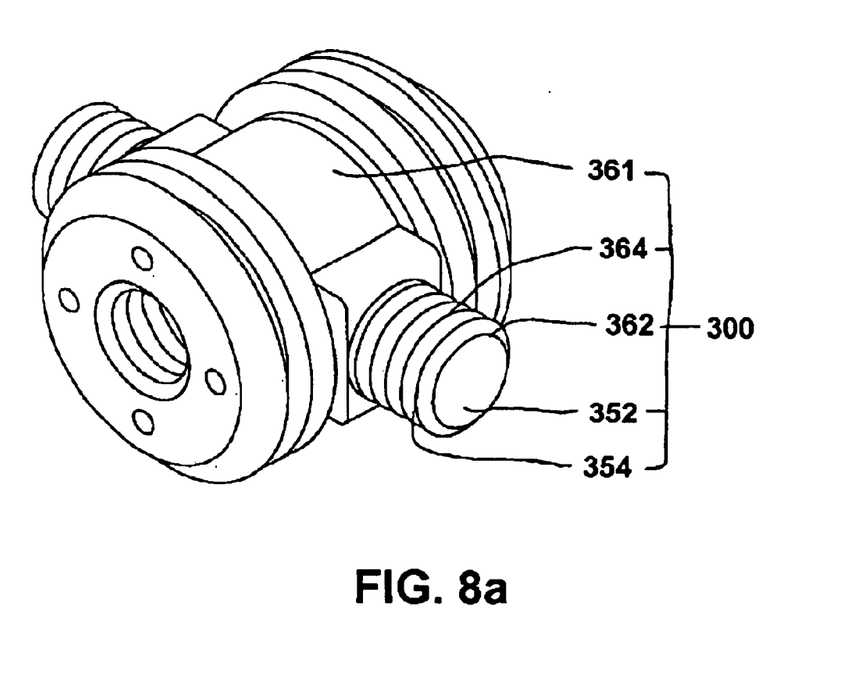
FIGS. 8a and 8b are sequential schematic view of the assembly of the principal components of the fifth preferred embodiment as shown in FIGS. 7a–7c.

In FIG. 7a, the side pieces 200 and 250 are provided with a threaded hole 218, 268. In FIG. 7b, the retrieval main body 100 is provided in the middle with a recess 150. FIG. 7c shows a joining means formed of the fitting ring members 350 and 360. 351, 352, 353 and 354 denote the fitting ring portion, the threaded rod portion, the protruded point and threads of the fitting ring member 350. The fitting ring member 360 is provided with a recessed hole opposite in location to the protruded point 353 for joining with the protruded point 353 after the fitting ring members 350 and 360 are both fit into the slot 150 of the retrieval main body 100 to form a joining means 300 as shown in FIG. 8a. 361, 362, and 364 denote the fitting ring portion, the threaded rod and threads of the fitting ring member 360. The side pieces 200 and 250 are then threaded onto the threaded rod portions 352 and 362 of the joining means 300, as shown in FIG. 8b.

Figure 9A:
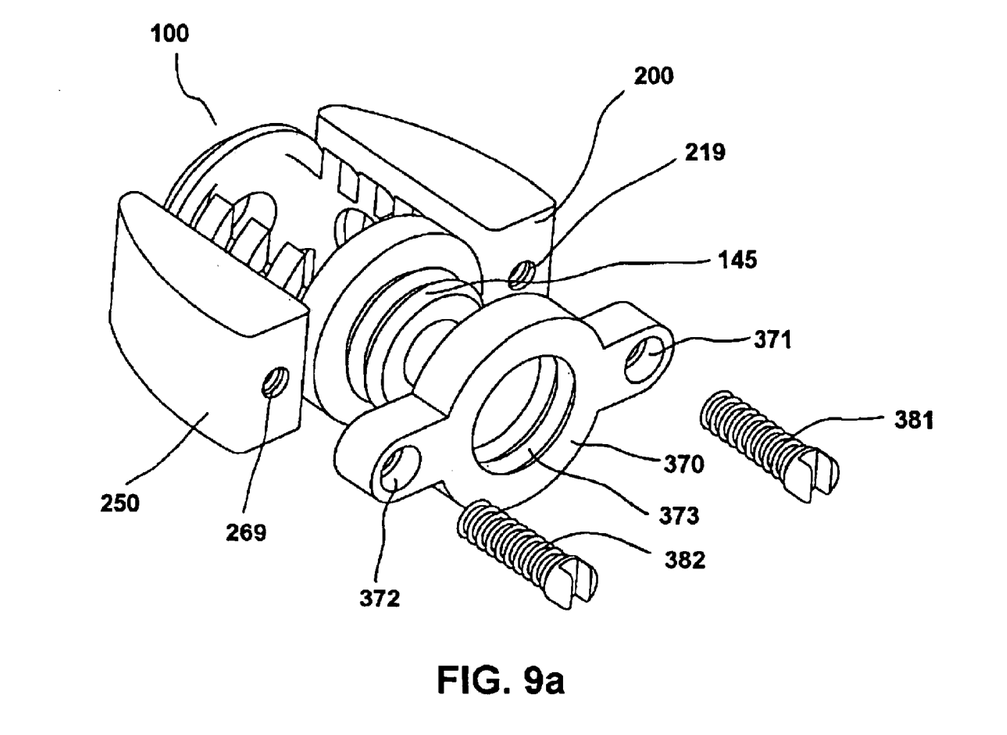
FIGS. 9a, 9b, and 9c are respectively an exploded view of a sixth preferred embodiment of the present invention, a front view of the sixth preferred embodiment in combination, and a top view of the sixth preferred embodiment in combination.
Figure 9B:
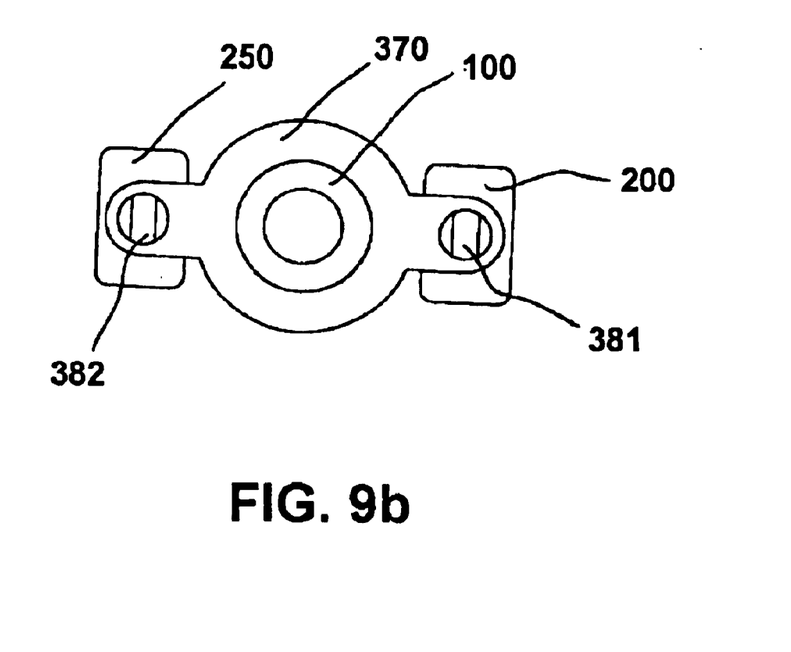
Figure 9C:
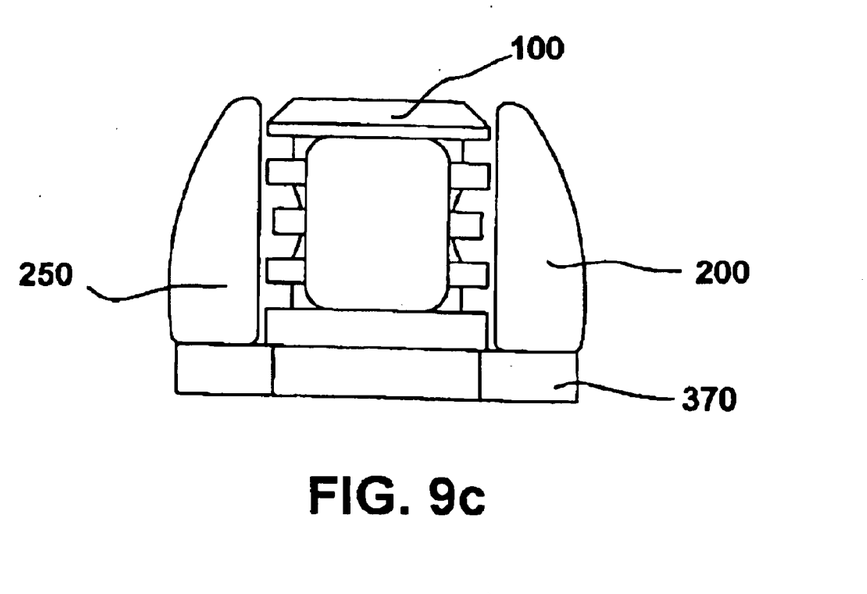
Figure 10A:
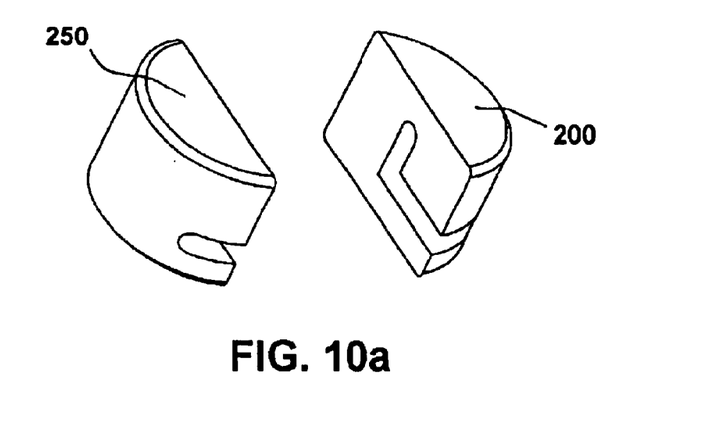
FIGS. 10a and 10b are schematic views of the principal components of a seventh preferred embodiment of the present invention.
Figure 10B:
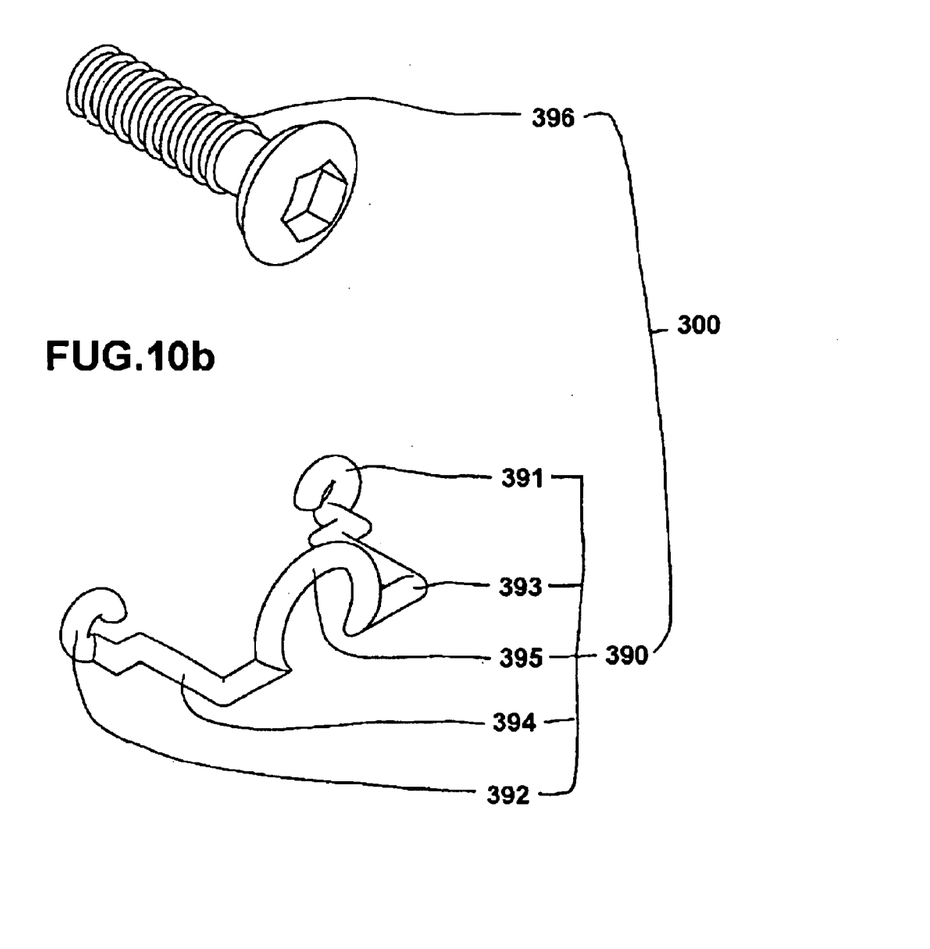
Figure 10C:
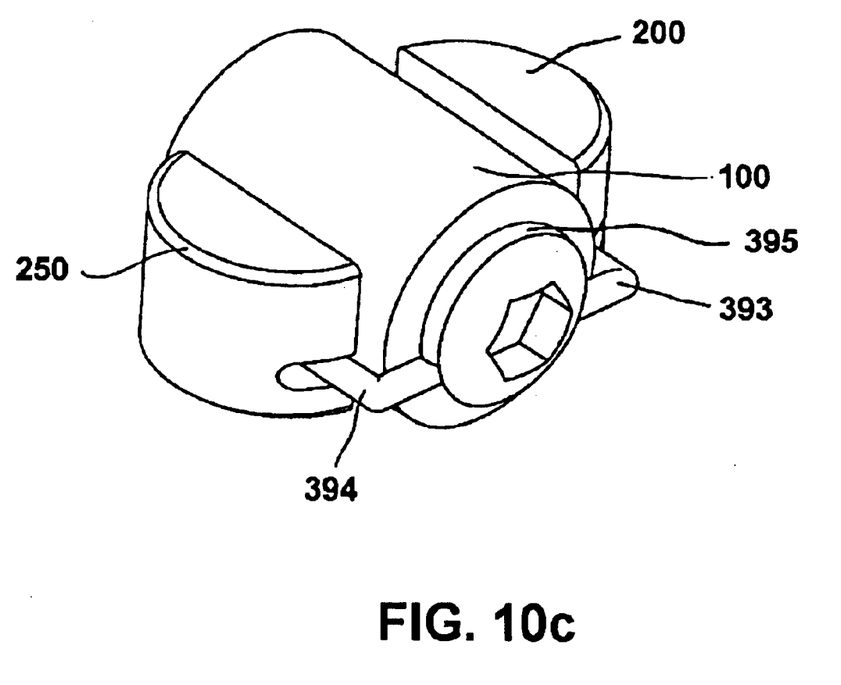
FIG. 10c shows a schematic view of the seventh preferred embodiment of the present invention in combination.

In FIG. 9a, the outer threads 145 of the retrieval main body 100 is engaged with the inner threads 373 of the joining fitting ring 370, and then screws 381 and 382 are threaded into the threaded holes 371 and 372 of the joining fitting ring 370 and the threaded holes 219 and 269 of the side pieces 200 and 250. FIGS. 9b and 9c are respectively the front view and the top view after assembly. The reference numerals in FIGS. 9b and 9c are similar in definition to those in FIG. 9a.

In FIGS. 10a–10c, 100, 200, 250, 300 are similar in definition to the like numerals of FIGS. 1a–1c. 390 and 396 denote the joining fitting strip and the joining screw of the joining means 300. 391(392). 393(394), and 395 denote the joining tail portion, the connection rod, the connection curved rod of the joining fitting strip 390.

Figure 8B:
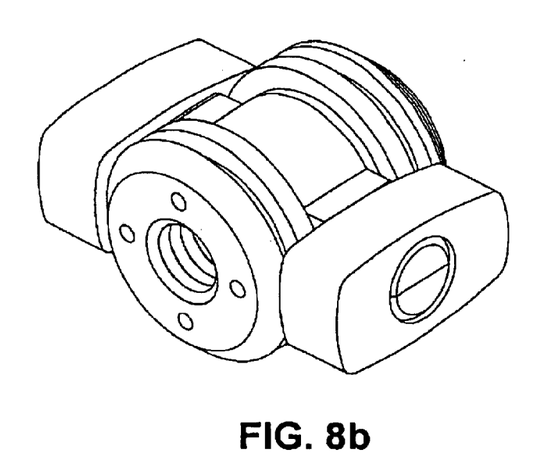

The side pieces and the retrieval main body of the spinal fixation and retrieval device of the present invention are preferably capable of turning (as shown in FIGS. 4a, 6d, and 8b) and/or twisting (as shown in FIGS. 5d, 6d, and 9a) in relation to each other. The word "turning" means the turning on the central axis of the retrieval main body. The word "twisting" refers to the one-end up-and-down motion of one side piece in relation to the planar surface which is formed by the central axes of the retrieval main body and the side pieces, as shown in FIGS. 5d and 6d. The up-and-down motion may be two-end up-and-down motion (one end up and other end down, as shown in FIG. 8b.)

The side pieces illustrated in the drawings are shown as being substantially located outside the retrieval main body.

What is claimed is:

1. A spinal fixation and retrieval device comprising:
   a retrieval main body;
   two side pieces, said two side pieces being joined together by a fitting means for fitting with said retrieval main body; and
   a joining means for pivotally joining substantially symmetrically said two side pieces to two points on two sides of said retrieval main body;
   wherein each one of said two side pieces is substantially smaller in height than said retrieval main body and is able to be rotated around an axis defined by said two points.

2. The device as claimed in claim 1, wherein said fitting means is a fitting ring.

3. A spinal fixation and retrieval device comprising:
   a retrieval main body;
   two side pieces; and
   a joining means for pivotally joining substantially symmetrically said two side pieces to two points on two sides of said retrieval main body;
   wherein each one of said two side pieces is substantially smaller in height than said retrieval main body and is able to be rotated around an axis defined by said two points;
   wherein said retrieval main body is joined with said joining means; wherein said two side pieces and said joining means are joined together by a connecting means such that said two side pieces are substantially not fastened directly with said retrieval main body.

4. The device as defined in claim 3, wherein said connecting means is a retaining means or a threading means.

* * * * *